(12) United States Patent
Joseph et al.

(10) Patent No.: US 11,602,648 B2
(45) Date of Patent: Mar. 14, 2023

(54) PROTECTIVE FACE SHIELD UTILIZING LAMINAR AIR FLOW

(71) Applicant: CZN, Inc., Chevy Chase, MD (US)

(72) Inventors: Daniel Mark Joseph, Windermere, FL (US); Jose Sebastian Apud, Chevy Chase, MD (US)

(73) Assignee: CZN, INC., Chevy Chase, MD (US)

( * ) Notice: Subject to any disclaimer, the term of this patent is extended or adjusted under 35 U.S.C. 154(b) by 0 days.

(21) Appl. No.: 17/722,185

(22) Filed: Apr. 15, 2022

(65) Prior Publication Data

US 2022/0331619 A1    Oct. 20, 2022

Related U.S. Application Data

(60) Provisional application No. 63/175,829, filed on Apr. 16, 2021.

(51) Int. Cl.
| | | |
|---|---|---|
| *A62B 18/00* | (2006.01) | |
| *A61L 9/20* | (2006.01) | |
| *A62B 7/10* | (2006.01) | |
| *A42B 3/04* | (2006.01) | |

(52) U.S. Cl.
CPC .............. *A62B 18/003* (2013.01); *A42B 3/04* (2013.01); *A61L 9/20* (2013.01); *A62B 7/10* (2013.01)

(58) Field of Classification Search
CPC .......... A62B 18/003; A42B 3/04; A42B 3/286
See application file for complete search history.

(56) References Cited

U.S. PATENT DOCUMENTS

| | | | | | |
|---|---|---|---|---|---|
| 3,649,964 | A | * | 3/1972 | Schoelz ................. | A61F 9/068 128/205.25 |
| 3,822,698 | A | * | 7/1974 | Guy ....................... | A42B 3/286 128/201.25 |
| 4,309,774 | A | * | 1/1982 | Guzowski ............. | A61F 9/068 2/906 |

(Continued)

FOREIGN PATENT DOCUMENTS

CN          211835878 U       11/2020

OTHER PUBLICATIONS

PCT International Search Report and Written Opinion dated Jul. 18, 2022, PCT International Application No. PCT/US22/25108, pp. 1-12.

*Primary Examiner* — Tajash D Patel
(74) *Attorney, Agent, or Firm* — Outlier Patent Attorneys, PLLC

(57) ABSTRACT

An airflow device configured for creating an air barrier includes a fan, a power source, a laminar assembly, and an attachment mechanism. The power source is coupled to the fan. The laminar assembly includes a plurality of tubes and is coupled to the fan so that air flow generated by the fan passes through the plurality of tubes to create the air barrier. The attachment mechanism attaches the laminar assembly to a user in a location near the user's head such that the air barrier created by the laminar assembly is positioned in front of the user's face. A plenum is positioned between the fan and the laminar assembly such that the air flow generated by the fan passes through the plenum and then through the laminar assembly. The airflow device acts as a face shield that protects the user from airborne contaminants and viruses.

19 Claims, 12 Drawing Sheets

(56) References Cited

U.S. PATENT DOCUMENTS

| | | | | |
|---|---|---|---|---|
| 4,549,542 | A * | 10/1985 | Chien | A62B 18/045 |
| | | | | D24/110.2 |
| 5,413,097 | A | 5/1995 | Birenheide et al. | |
| 8,756,715 | B1 * | 6/2014 | Moffitt, Jr. | A42B 3/24 |
| | | | | 2/171.3 |
| 11,166,497 | B1 * | 11/2021 | Wilson | A41D 13/0025 |
| 2007/0089221 | A1 * | 4/2007 | Manzella | A61B 90/50 |
| | | | | 2/456 |
| 2007/0272244 | A1 | 11/2007 | Witmer | |
| 2016/0236014 | A1 | 8/2016 | Ehler et al. | |
| 2020/0206446 | A1 | 7/2020 | Blaxland | |
| 2021/0378346 | A1 * | 12/2021 | Abghari | A61F 9/045 |
| 2022/0118288 | A1 * | 4/2022 | Space | B01D 46/0047 |
| 2022/0126126 | A1 * | 4/2022 | Clack | A61L 9/22 |

\* cited by examiner

PROTECTIVE FACE SHIELD UTILIZING LAMINAR AIR FLOW

CROSS-REFERENCE TO RELATED APPLICATIONS

This application claims priority to U.S. Provisional Patent Application No. 63/175,829 filed on Apr. 16, 2021, the contents of which are incorporated herein by reference.

BACKGROUND

Field of the Art

This disclosure relates to an airflow device that creates an invisible air barrier face shield. The airflow device is configured to be worn on the user's head and create an air shield in front of the user's face.

Discussion of the State of the Art

Face masks and face shields have been around for many years. Upon the arrival of the COVID-19 coronavirus, they have become critical in our safety to stop the spread of the virus. Many public places recommended their use, and some require it. Everywhere, from grocery stores, to gas stations, to schools, to office buildings, even theme parks and museums require guests to wear a face mask at all times.

Face masks work by inhibiting or blocking airflow to the nose and mouth. Since we breathe hot humid air, cloth, paper, and other fabric face masks are very uncomfortable and if not washed very often, can even harbor bacteria. These masks and shields also have a medical look to them that can be scary to young children who look to the human face for all sorts of social cues. Face masks are extremely uncomfortable to wear, especially while working and doing extracurricular activities outside.

There are several disadvantages with these face masks. Even a face mask made of a simple cotton material can cause eye glasses to fog up, make the user hot, and cause face irritations ("maskne"). Further, a face mask covers the user's mouth, which makes social interaction to facial cues impossible. Another disadvantage is that face masks cannot be worn when eating or drinking, which makes those activities even riskier due to the user not being protected from viruses while the face mask is removed. Still further, face masks are uncomfortable and may make a user (e.g., a user experiencing claustrophobia or asthma) feel as if they are having difficulty breathing. The elastic ear loops of the face mask may hurt a user's ears.

Thus, there is a need for a device that is an alternative to a conventional face mask while also effectively protecting the user from airborne viruses.

SUMMARY

A protective face shield in accordance with the present invention is configured to provide a curtain, or wall, of air, which flows in front of the user's face. The protective face shield does not use fabric, paper, or cloth to block pathogens from being projected out of the user's mouth into a room, or conversely, pathogens in the room from floating to the user's face. The laminar air flow provided by the protective face shield is quiet, invisible, and just as effective as a fabric face covering.

The protective face shield in accordance with the present invention is advantageous over conventional fabric face shields because the protective face shield allows the user to have their face completely uncovered while providing the same level of protection as a face mask to the user and the people around the user. Since this device is worn on the head like a visor, it is comfortable and leaves the face completely unblocked and untouched. Also, since the unit creates its protection via a curtain of air, it can be worn while eating and drinking, and provide the same protection as a fabric mask.

Another advantage of the protective face shield in accordance with the present invention is that it offers the same level of protection as a face mask without having to put something on one's face or even cover one's face.

The protective face shield is a wearable, compact unit. In one example, the laminar airflow generated by the protective face shield may be scaled up and used as a physical barrier, just like plexiglass used today at cashier's stations in stores. The unit can function in the current downward facing configuration but can easily be configured to work pointed upward at a larger scale.

In one embodiment of the present invention, an airflow device configured for creating an air barrier includes at least one fan. The device may include two or more fans. The airflow device further includes a power source coupled to the at least one fan. The power source may, for example, include a rechargeable battery. Still further, the airflow device includes a laminar assembly comprising a plurality of tubes. The laminar assembly is coupled to the at least one fan so that air flow generated by the at least one fan passes through the plurality of tubes to create the air barrier. The airflow device further includes an attachment mechanism for attaching the airflow device to a user's head such that the air barrier is positioned in front of the user's face. The attachment mechanism may be configured to attach the airflow device to a user's forehead, chest, or neck, or to a brim of a hat. For example, the attachment mechanism may be a strap, a clip, or a helmet. The airflow device may also include a plenum disposed between the at least one fan and the laminar assembly such that the air flow generated by the at least one fan passes through the plenum and then through the laminar assembly. Each one of the tubes in the laminar assembly may have a diameter between 0.05 inches and 0.8 inches. When the airflow device is attached to the user, the at least one fan may be positioned above the user's head and the laminar assembly may be positioned against the user's forehead. Alternatively, when the airflow device is attached to the user, the at least one fan may be positioned adjacent to the user's neck and the laminar assembly may be positioned below the user's chin. The airflow assembly may further include a filter for filtering the air used to create the air barrier. The airflow device may further include a fan speed adjustment mechanism, an anemometer, and/or a UV light emitter configured for purifying the air used to create the air barrier. The airflow device may further include a plastic shield adjacent to the air barrier and/or a copper mesh disposed in an intake of the fan.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

Figure 1:
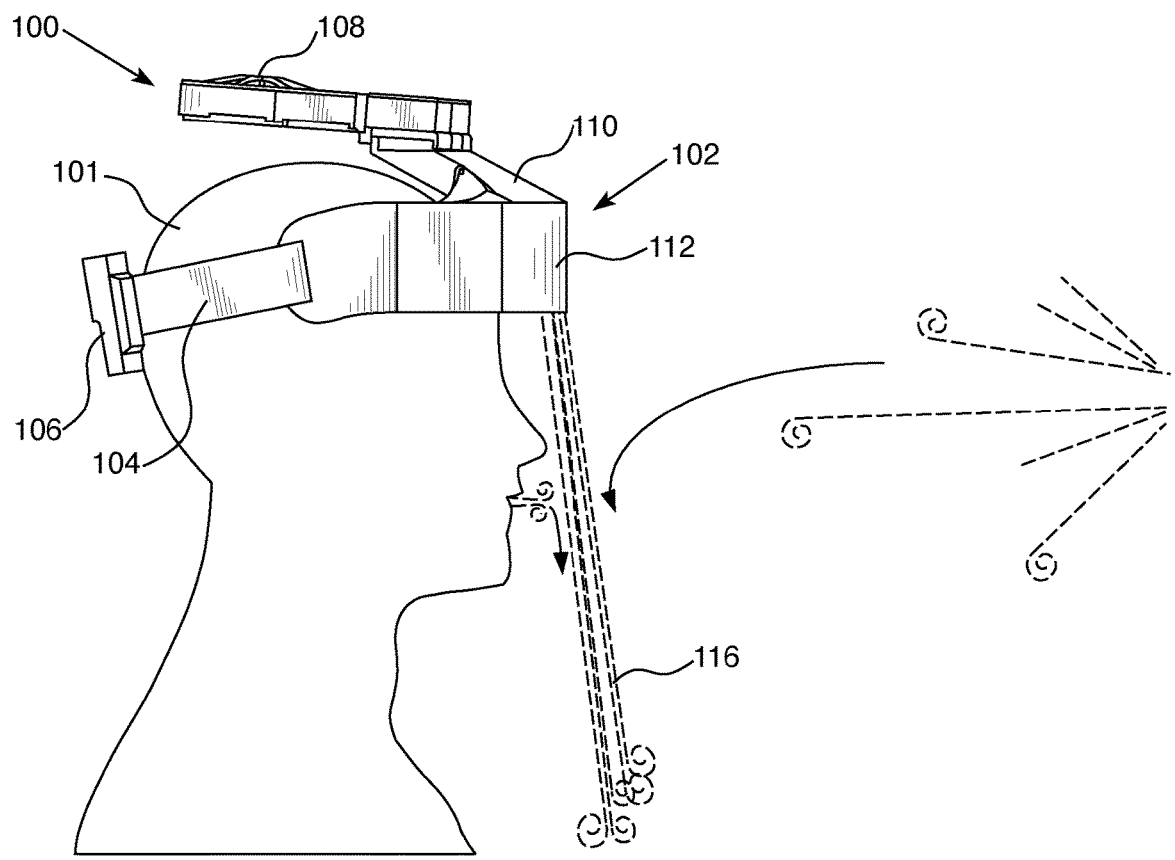
FIG. 1 is a side view of an airflow device in use attached to a user's head, in accordance with an embodiment of the present invention.

A protective face shield of the present invention includes an airflow device configured for creating an invisible air barrier in front of a user's face. The airflow device may be worn on the user's head and, when activated, creates an air curtain in front of the user's face. The airflow device includes fans and a laminar assembly. The fans generate air flow that passes through the laminar assembly, which organizes the air flow into an air shield having a desired shape and air flow velocity that is sufficient to protect the user from airborne particles and viruses. The fans and laminar assembly are coupled to each other and to an attachment mechanism for attaching the device to the user's head.

The invention is described by reference to various elements herein. It should be noted, however, that although the various elements of the inventive apparatus are described separately below, the elements need not necessarily be separate. The various embodiments may be interconnected and may be cut out of a singular block or mold. The variety of different ways of forming an inventive apparatus, in accordance with the disclosure herein, may be varied without departing from the scope of the invention.

Generally, one or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices and parts that are connected to each other need not be in continuous connection with each other, unless expressly specified otherwise. In addition, devices and parts that are connected with each other may be connected directly or indirectly through one or more connection means or intermediaries.

A description of an aspect with several components in connection with each other does not imply that all such components are required. To the contrary, a variety of optional components may be described to illustrate a wide variety of possible embodiments and in order to more fully illustrate one or more embodiments. Similarly, although process steps, method steps, or the like may be described in a sequential order, such processes and methods may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, or method is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Alternate implementations are included within the scope of various embodiments in which, for example, functions may be executed out of order from that shown or discussed, including substantially concurrently or in reverse order, depending on the functionality involved, as would be understood by those having ordinary skill in the art.

Overview

The apparatus of the present invention is an airflow device configured for creating an invisible air barrier in front of a user's face. The airflow device may be worn on the user's head and, when activated, creates an air curtain in front of the user's face. The airflow device includes fans and a laminar assembly. The fans generate air flow that passes through the laminar assembly, which organizes the air flow into an air shield having a desired shape and air flow velocity that is sufficient to protect the user from airborne particles and viruses. The fans and laminar assembly are coupled to each other and to an attachment mechanism for attaching the device to the user's head.

Apparatus

Figure 2:
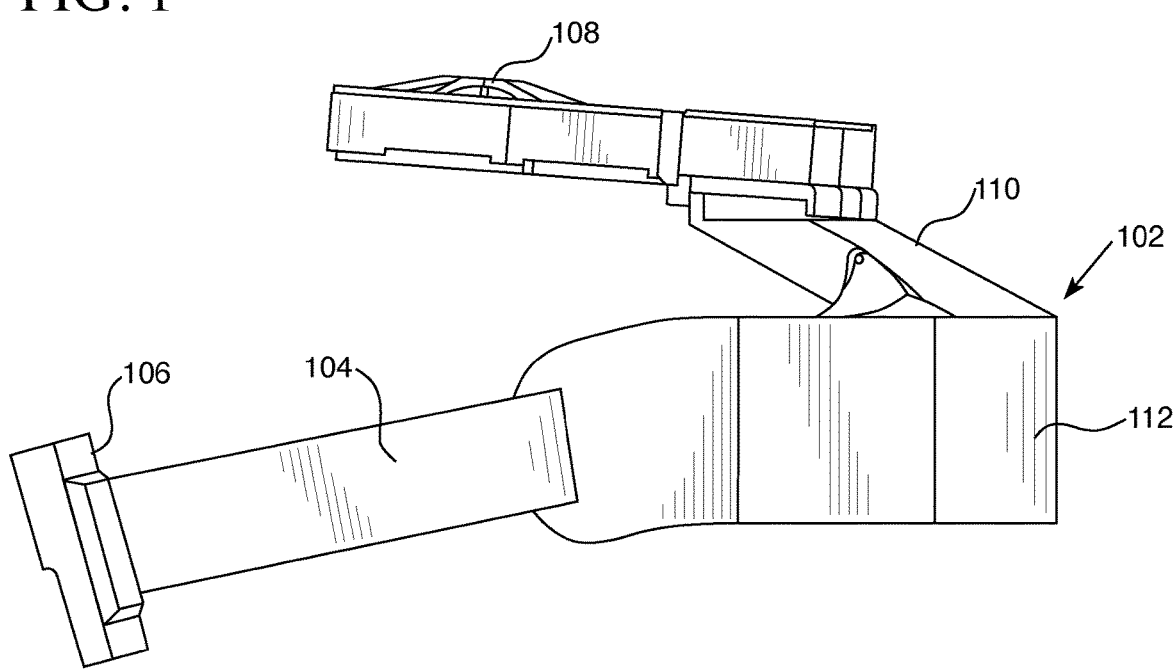
FIG. 2 is a side view of an airflow device, in accordance with an embodiment of the present invention.

A laminar air flow device 100 configured for creating an invisible air barrier 116 in accordance with the present invention is depicted in FIGS. 1 and 2. The face shield 100 includes a forehead assembly 102 that is configured to be attached to a user's head 101 using an attachment mechanism 104. The face shield 100 also includes a battery module 106 that is operatively coupled to the forehead assembly 102.

The attachment mechanism 104 is an adjustable strap for easy attachment and removal from the user's head 101. The strap 104 may be stretchy and/or may be attached to the user's head 101 with a buckle, snap, button, hook and loop closure, or the like.

Figure 3:
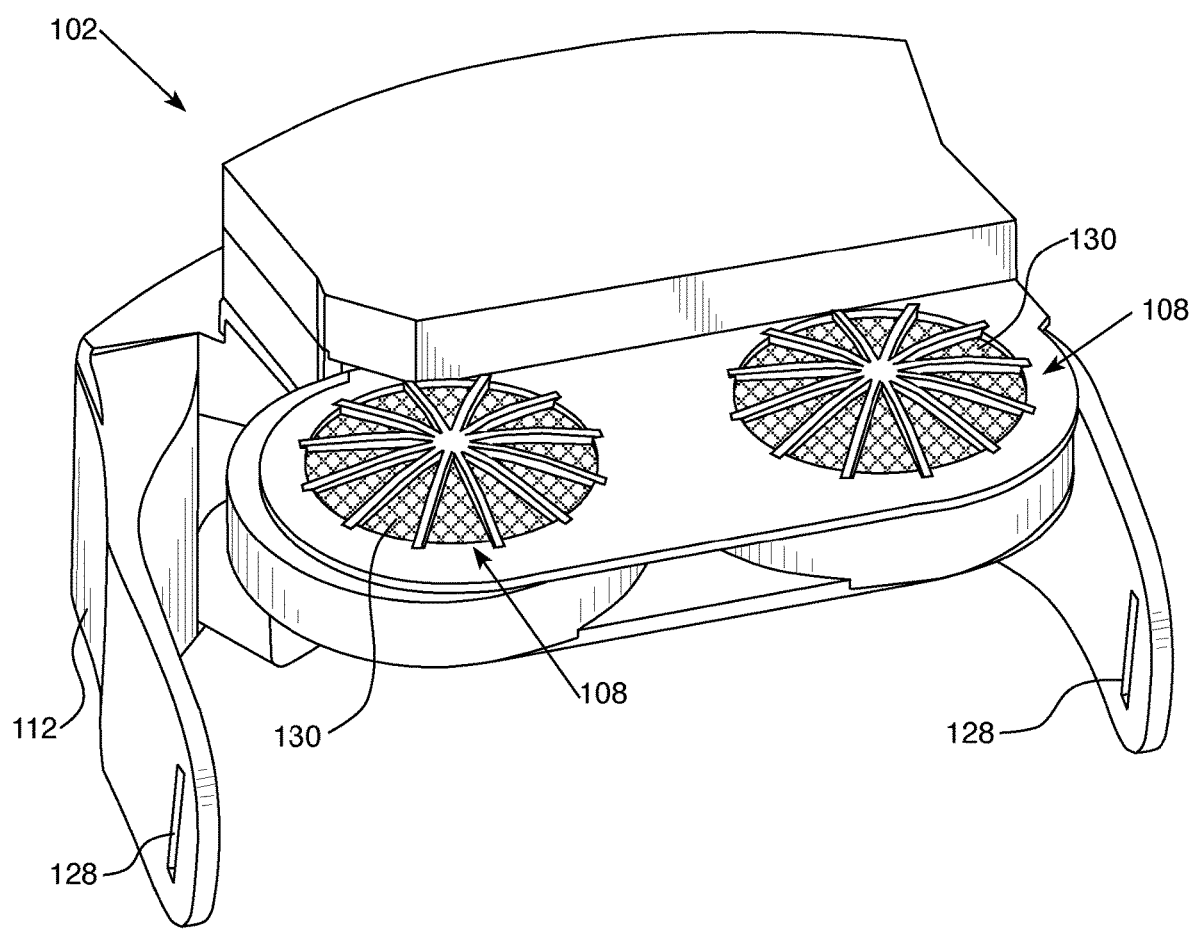
FIG. 3 is a perspective view of a forehead assembly of an air flow device, in accordance with an embodiment of the present invention.
Figure 4:
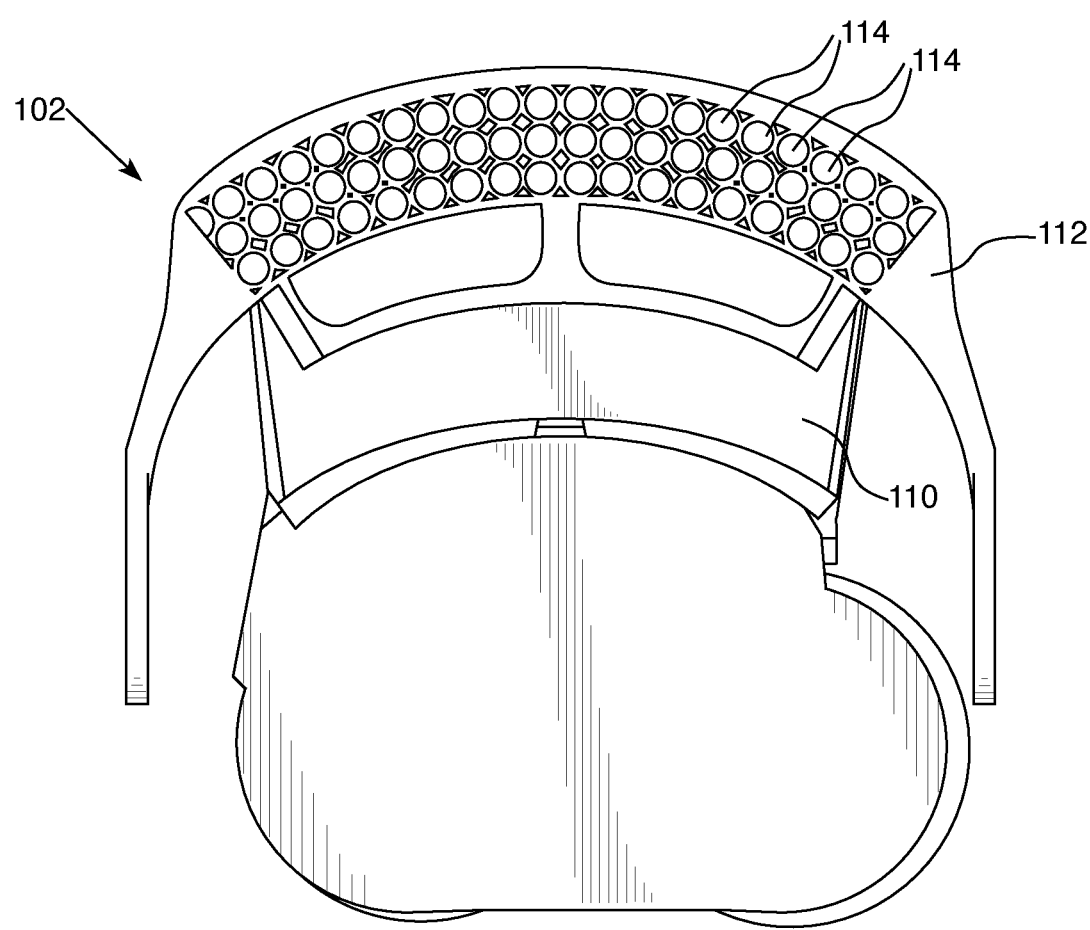
FIG. 4 is a bottom view of a forehead assembly of an airflow device, in accordance with an embodiment of the present invention.

The forehead assembly 102 is shown in more detail in FIGS. 3 and 4. The forehead assembly 102 includes fans 108, a plenum 110, and a laminar assembly 112 having an array of tubes 114 for directing the air flow. The plenum 110 is a hollow space that collects the air generated by the fans 108 and distributes that air across the laminar assembly 112. That is, the air generated by both fans 108 flows into one volume in the plenum 110.

The forehead assembly 102 may be made with injection molded plastic as one or two pieces. Slots 128 in the forehead assembly 102 are configured to engage with the attachment mechanism 104. Alternatively, the forehead assembly 102 may be made of other strong, rigid materials and may include a different connection mechanism for coupling to the attachment mechanism 104. For example, the forehead assembly 102 may be made of metal, wood, fiberglass, or the like, or any combination thereof. Instead of slots 128, the forehead assembly 102 may have another type of connection mechanism, such as loops, snaps, clips, buttons, hook and loop closures, or the like.

In this example, the forehead assembly 102 includes two fans 108, but the invention is not limited to two fans. Indeed, the forehead assembly 102 may include only a single fan, or may have three or more fans. Air is drawn into the forehead assembly 102 through the fan intake and is accelerated by the fans 108 through the plenum 110, and out through the laminar assembly 112 to form a barrier 116 (shown in FIG. 1) of laminar air flow in front of the user's face.

When the fans 108 are on, the air flow generated by the fans 108 is extremely turbulent. If this air was simply ducted in front of the user's face, it would be a frenetic cloud and cause anything flowing to or from the user's nose and mouth to spiral and fly in every direction. There would be no predictability as to where the air would flow or where the pathogens would fly. In order to force the air to flow in a desired path, the laminar assembly 112 includes small tubes 114 (shown in FIG. 4) packed into an array through which the air flow generated by the fans 108 passes. In this manner, the combined air flow volume from the two fans 108 is straightened out, and organized into a sheet 116 (shown in FIG. 1). The laminar assembly 112 directs the air molecules to move in the exact same direction in an organized manner. Since the laminar assembly 112 has an arc shape substantially similar to the human forehead in plan view, the laminar air sheet 116 flows in that shape down in front of the user's face, wrapping around in front of the nose, eyes, and mouth. The organized laminar air sheet 116 forms the shape of a plastic full-face shield, yet it is air. Since the air is high volume, anything flowing from the ambient space or room toward the user hits the sheet of air 116 before it can touch or enter the user's face and is blown straight down to the floor. Similarly, anything that comes out of the user's mouth or nose stops and is blown straight down to the floor once it enters the organized sheet 116 of laminar air flowing in front of the user's face. This effectively protects the wearer and the people in the room or space around the wearer from sharing pathogens, without putting a plastic or other physical barrier in front of the user's face.

However, a physical barrier may still be desired for protecting the user from anything that may penetrate the air shield. For example, as shown in FIG. 6, a plastic shield 140 may be added to the airflow device 100 in order to protect the user from blood spatter, sputum, or the like. In the example shown in FIG. 6, the airflow device 100 includes both the plastic shield 140 and the air shield created when the fans 108 are on. The air shield generated by the device 100 is in front of the user's face and is positioned between the user's face and the plastic shield 140.

Referring back to FIG. 4, the tubes 114 in the laminar assembly 112 may have a diameter of about 0.05 inches to 0.8 inches, and the number of tubes 114 in the array depends on the diameter of the tubes 114. In one example, the tubes 114 have a diameter of 0.2 inches and the array includes 54 tubes 114. The tubes 114 preferably have a length of at least 1.5 inches. Although the tubes 114 are depicted as having a circular cross-section, it will be readily appreciated by one of ordinary skill in the art that other cross-sectional shapes are possible, such as square, hexagon, octagon, pentagon, triangular, or the like. The array of tubes 114 is arranged in an arc shape in order to form an air shield having an arc shape that will protect the front and sides of the user's face.

A copper mesh 130 (shown in FIG. 3) may be disposed between the ambient air and the fans 108. That is, the copper mesh 130 may be positioned at the intake of the fans 108. The copper mesh 130 provides the antibacterial and antiviral qualities of copper to the air flowing into the unit 100.

Figure 7:
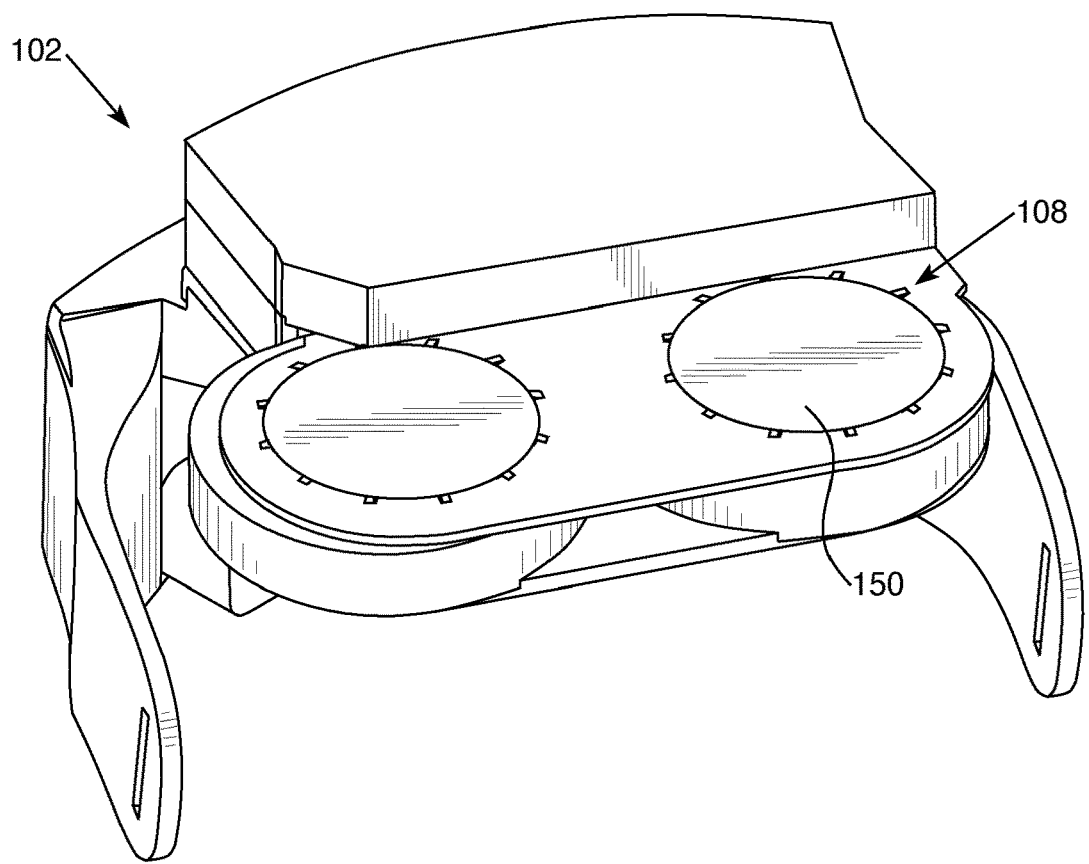
FIG. 7 is a perspective view of a forehead assembly that includes air filters attached to the fan intake, in accordance with an embodiment of the present invention.

Additionally or alternatively, air filters 150 may be positioned over the fan intakes, as shown in FIG. 7. The air filters 150 are thus easily accessible and may be replaceable. In this manner, the air is filtered before passing through the fans 108, thereby increasing the quality of air that forms the air shield 116. Additionally or alternatively, the air may be filtered, sanitized, purified, or otherwise treated in some manner before exiting the laminar assembly 112 to create the air barrier 116. Examples of air treatment devices are discussed in more detail below with reference to FIGS. 8, 11, and 17. Other air treatment devices that may be incorporated into the airflow device 100 may include electrostatic precipitators, impactors, or the like.

Figure 5:
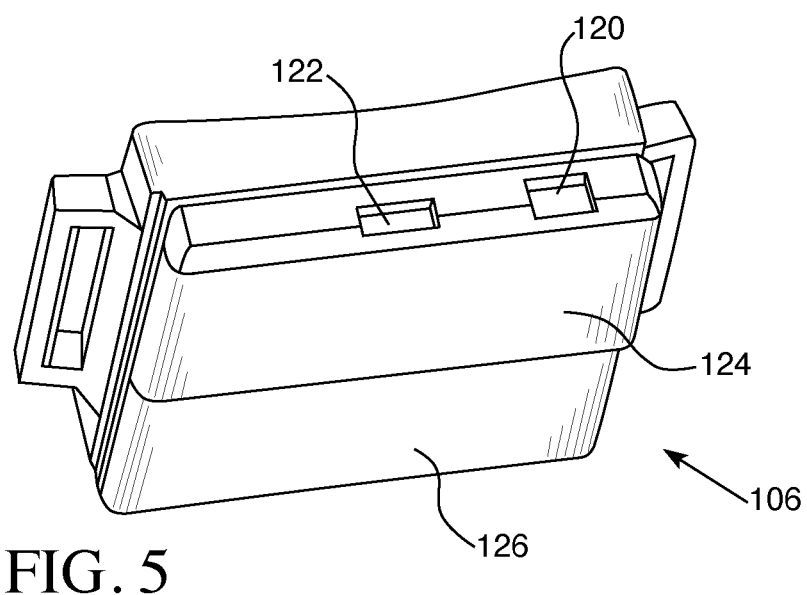
FIG. 5 is a perspective view of a battery module of an airflow device, in accordance with an embodiment of the present invention.
Figure 6:
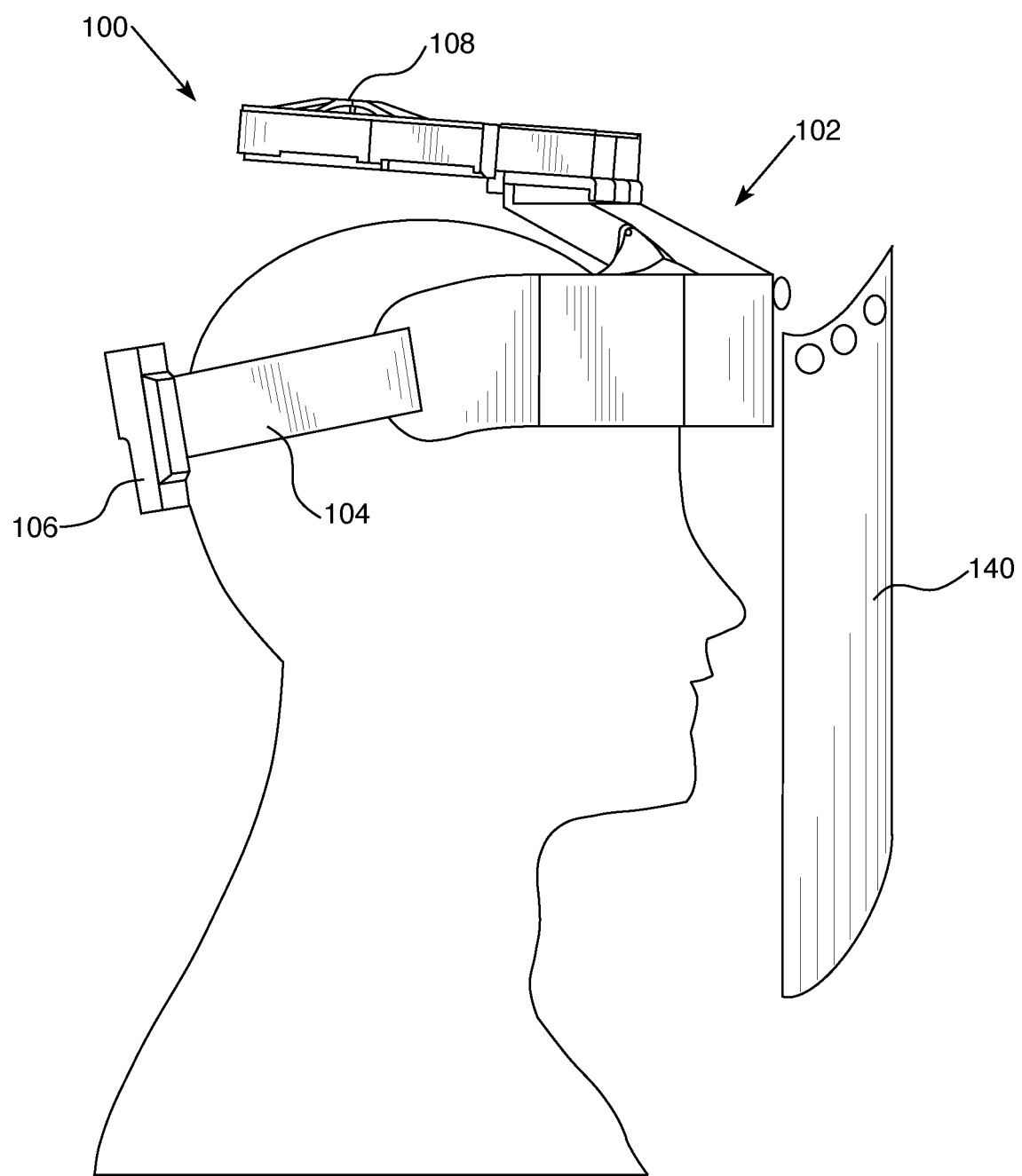
FIG. 6 is a side view of an airflow device that includes a solid shield, in accordance with an embodiment of the present invention.

The battery module 106, shown in more detail in FIG. 5, may be any conventional battery module capable of providing power to the fans 108. The battery module 106 is operatively coupled to the fans 108 through wires in or along the attachment mechanism 104. The battery module 106 is preferably lightweight and rechargeable. The battery module 106 may be made of injection molded plastic or other similar sturdy, rigid materials. The invention is not limited to the battery module 106 being attached to the attachment strap 104. It will be well understood by one of ordinary skill in the art that the battery module 106 may alternatively be attached to the forehead assembly 102 or any other convenient location on the face shield 100. In one example, the battery module 106 includes a power switch 120, a charging port 122, a circuitry compartment 124, and a battery compartment 126.

In one example, the battery in the battery compartment 126 is a lithium polymer battery, and the circuitry compartment 124 houses a charge controller and a step up boost converter. For example, the battery in the battery compartment may be a 3.7V, 2300 mAh lithium polymer battery. When 5V DC power from a micro USB connector, USB C connector, or the like, is connected to the charging port 122 in the battery module 106, that 5V power must be regulated down to charge the 3.7V lithium polymer battery. This battery can only supply 3.7V so there is a voltage boosting and regulation circuit in the battery module 106 that boosts the 3.7V up to the needed 12V DC needed to power the fans 108.

The regulated power from the battery in the battery compartment 126 is sent through two thin wires (e.g., 26 awg wires) along the adjustable head strap 104 and wired into the two blower fans 108. In one example, the fans 108 are each 28 decibels (dB) in sound level, and have a flow rating of 8.5 cubic feet per minute (CFM). As such, the two fans 108 together create an air flow of approximately 17 CFM. However, it will be well understood by one of ordinary skill in the art that the fans 108 may have a higher air flow rating and sound level. The 8.5 CFM, 28 dB, 12V fans 108 were selected based on the noise, air volume, and overall size. The selected fans 108 are also very energy efficient, which helps the battery last longer.

It will be well understood by one of ordinary skill in the art that the invention is not limited to the battery and fan configuration examples given above. For example, the face shield 100 of the present invention may include a larger capacity battery and larger and/or more powerful fans. Further, the face shield 100 may alternatively run on a different power source or a different type of battery, such as alkaline batteries, NiCd batteries, or the like.

Figure 8:
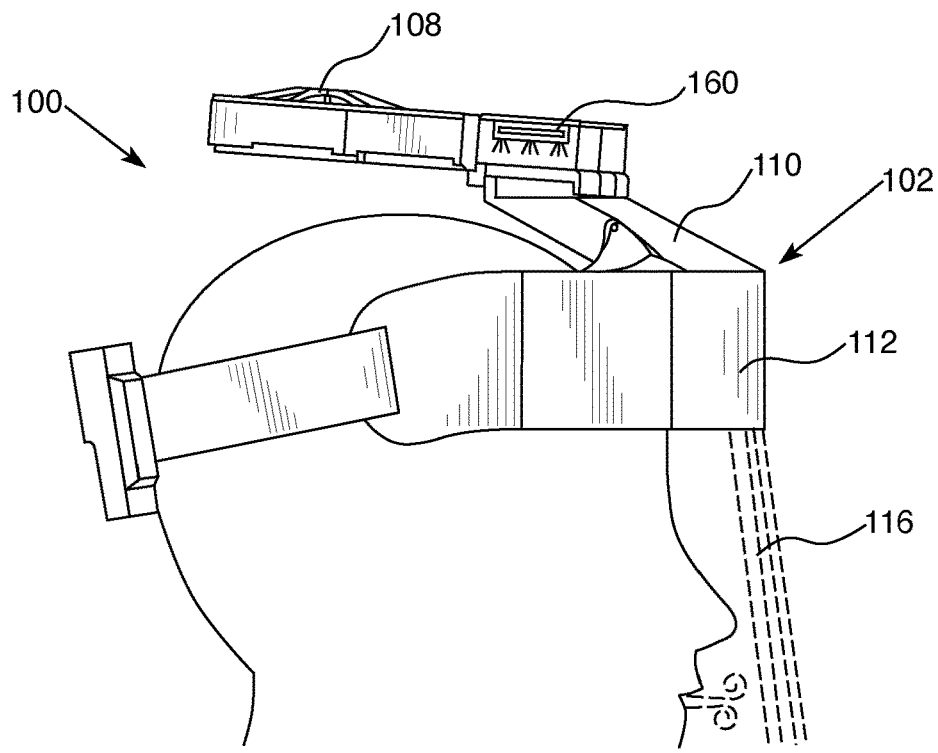
FIG. 8 is a side view of an airflow device in use attached to a user's head and having an air ionizer, in accordance with an embodiment of the present invention.

In one example, shown in FIG. 8, the air shield device 100 additionally includes an air ionizer 160. The air ionizer 160 improves air quality and eliminates unwanted particles from the air before the air flows into the laminar assembly 112. In this manner, the air that forms the air shield 116 is relatively high quality air compared to the ambient air.

Figure 9:
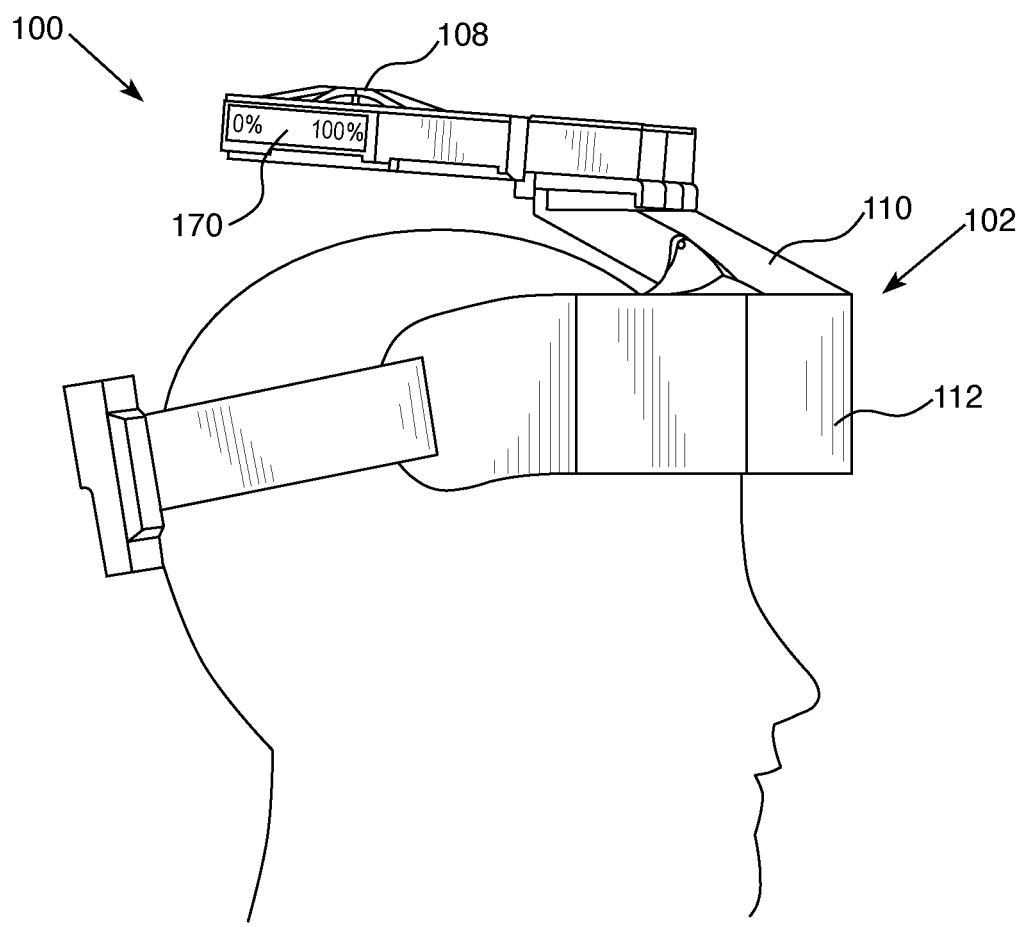
FIG. 9 is a side view of an airflow device in use attached to a user's head and having a battery life indicator, in accordance with an embodiment of the present invention.
Figure 10:
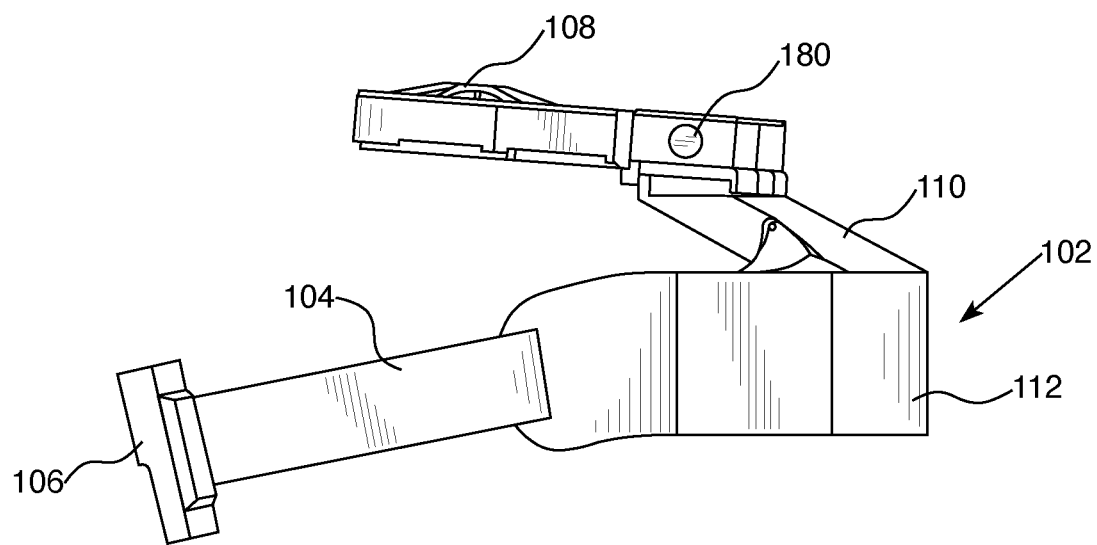
FIG. 10 is a side view of an airflow device having a fan speed adjuster, in accordance with an embodiment of the present invention.

In another example, shown in FIG. 9, the air shield device 100 additionally includes a battery indicator and/or wind speed indicator 170. The battery indicator 170 allows the user to easily see how much energy is left in the battery. Alternatively, a wind speed indicator 170 allows the user to easily see what the wind speed of the ambient air is, and adjust the face shield accordingly. For example, in a high wind environment, the user may want to increase the fan speed. The wind speed indicator may include an ultrasonic wind speed sensor, an infrared wind speed sensor, a microphone, or the like. As shown in FIG. 10, the air shield device 100 may include a fan speed adjustment button or knob 180. A user is able to increase or decrease the speed of the fans 108, and thus the flowrate of the air creating the air shield 116.

Figure 11:
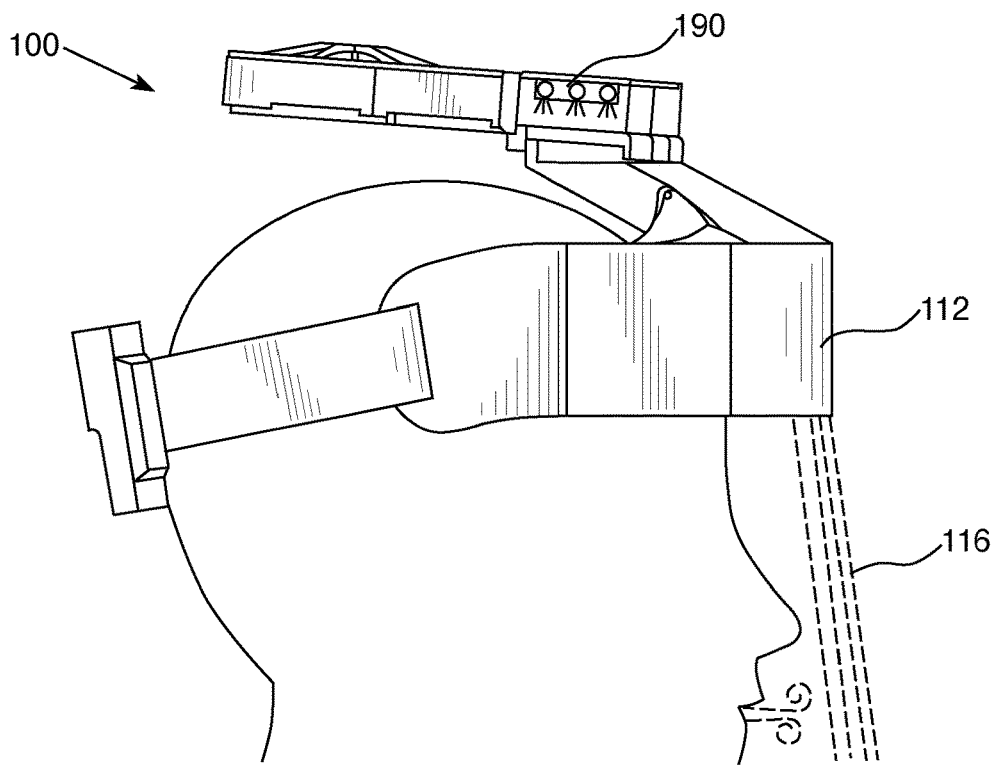
FIG. 11 is a side view of an airflow device in use attached to a user's head and having a UV light, in accordance with an embodiment of the present invention.

In still another example, shown in FIG. 11, the air shield device 100 additionally includes a UV light 190 for sanitizing the air before the air enters the laminar assembly 112. The UV light 190 may be positioned between the fan and the laminar assembly 112. In this manner, the air that forms the air shield 116 is sanitized relative to the ambient air.

Figure 12:
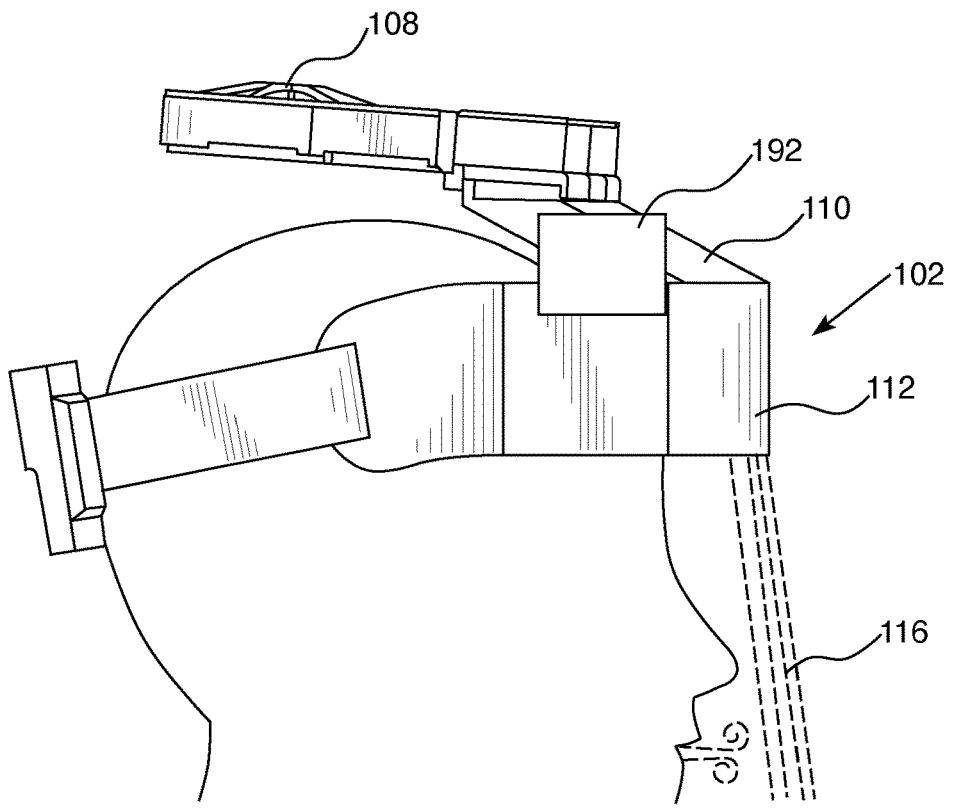
FIG. 12 is a side view of an airflow device in use attached to a user's head and having an anemometer, in accordance with an embodiment of the present invention.

In yet another example, shown in FIG. 12, the air shield device 100 additionally includes an anemometer 192. The anemometer 192 is configured to measure the wind speed of the ambient air. The anemometer 192 may be a vane, sonic, or thermal anemometer. The air shield device 100 may be configured to automatically adjust the speed of the fans 108 based on measurements from the anemometer 192. Alternatively, as discussed above with reference to FIG. 10, the user may be able to manually adjust the speed of the fans 108.

When entering a public space, the user would slip the unit 100 on their forehead and flip the switch 120 to on. Once the switch 120 is placed "on" the fans 108 will start up, which creates an invisible barrier 116 in front of the face. The user can keep the unit 100 on all day and while they eat and drink, both inside and outside. Then when finished with the social outing, the unit 100 gets plugged into a 5V mini USB phone charger to charge back up for the next use.

This device 100 can additionally be used to cool one's face on a dry, hot day. Having a continuous flow of clean directional air cascading in front of one's face has a cooling effect. The device 100 similarly could be used in a smoky environment. If more air volume was achieved by larger fans with higher flow rates, the device 100 could help firemen in a rescue or help the people needing rescue from smoke blowing into their face. Similarly, the device may be used to protect the user from low air quality environments, such as polluted air or air that is smoke-filled due to wildfires.

The current invention is a wearable compact unit 100, but if it were scaled up could act as a physical barrier, just like plexiglass used today at cashier's stations in stores. The unit 100 can function in the current downward facing configuration but can easily be configured to work pointed upward.

Figure 13:
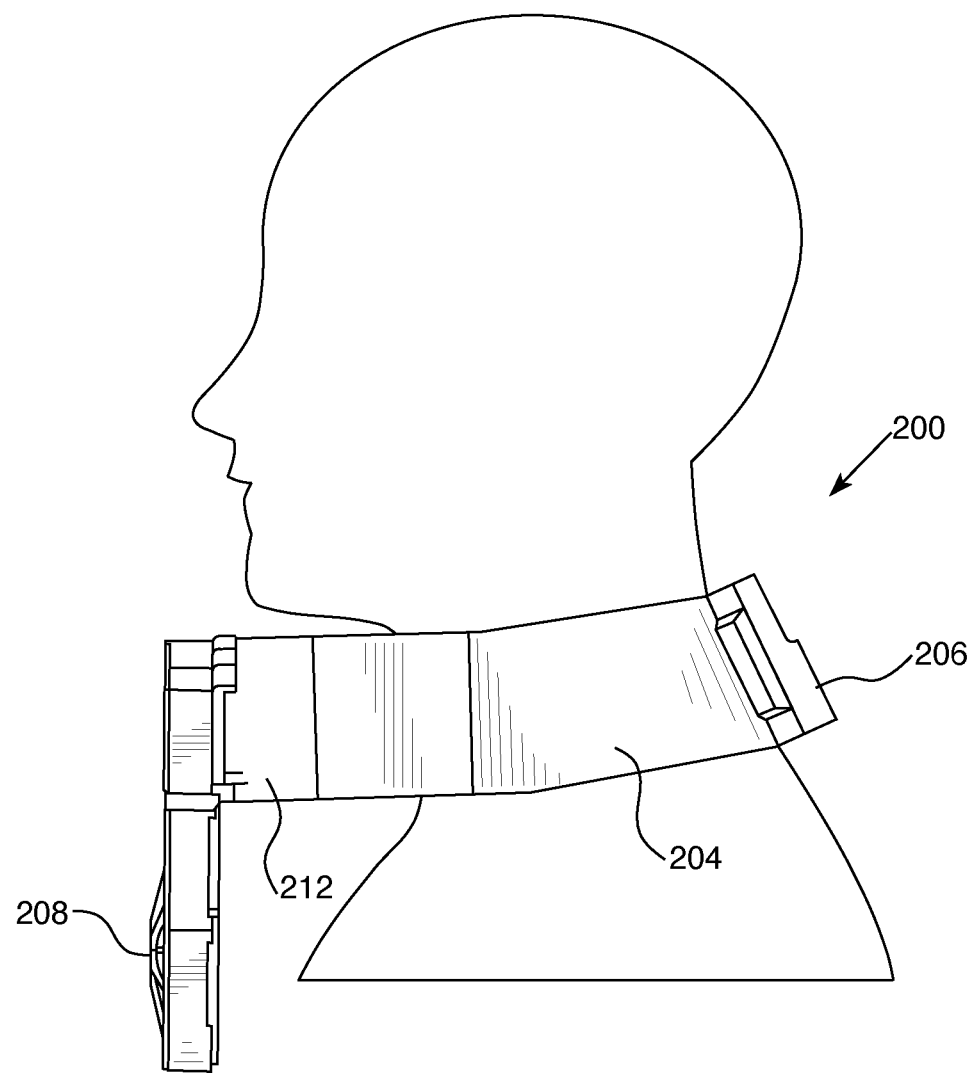
FIGS. 13 and 14 are side views of an airflow device in use attached to a user's neck, upper chest, or upper back, and having fans in the front and the back, respectively, in accordance with embodiments of the present invention.

For example, the air shield device may be configured to form an air shield that flows upward rather than downward. That is, the air forming the air shield flows from the user's chin area towards the user's forehead. In one embodiment, shown in FIG. 13, an air shield device 200 includes fans 208 positioned under the user's chin adjacent to the user's upper chest area. The fans 208 are coupled to a laminar assembly 212 that forces the air generated by the fans 208 into a laminar air curtain in front of the user's face. The air shield device 200 further includes a power source 206 and an attachment mechanism 204 configured to attach to the user's neck.

Figure 14:
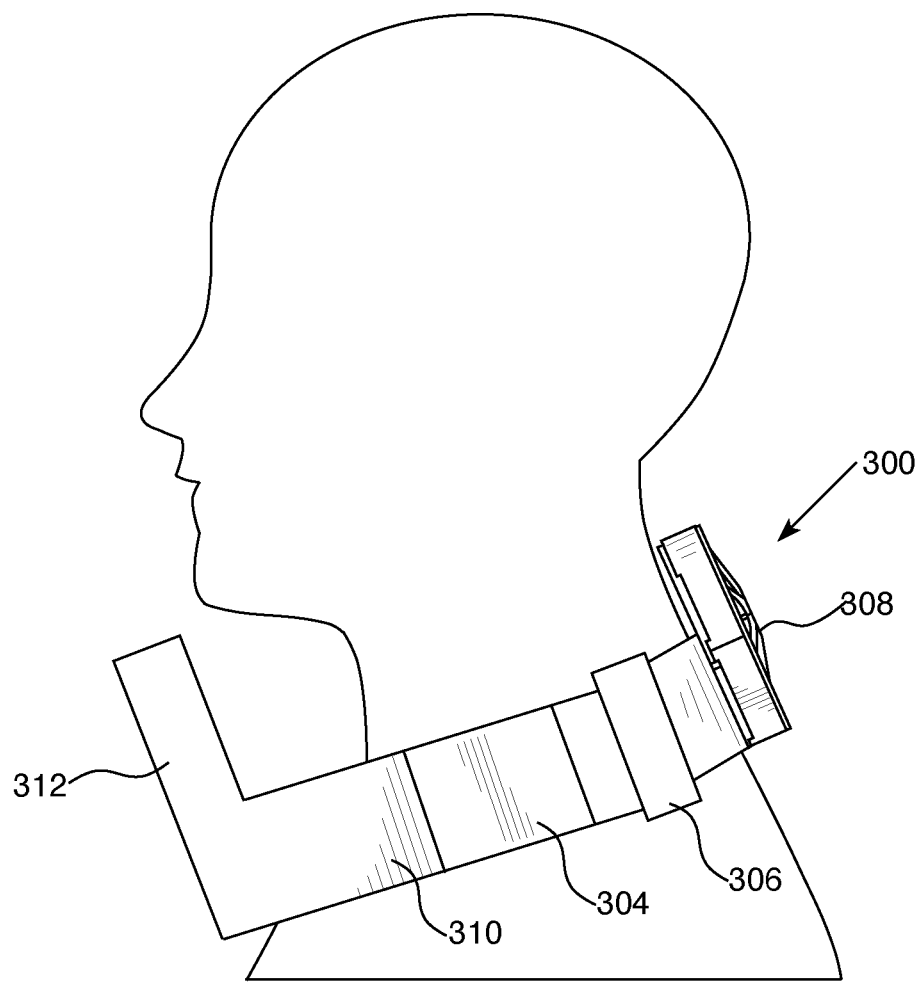

Similarly, the air shield device 300 shown in FIG. 14 includes fans 308, a power source 306, an attachment mechanism 304, and a laminar assembly 312. The fans 308 in the air shield device 300 are positioned behind the user rather than in front of the user. The air shield device 300 further includes a plenum 310 disposed between the fans 308 and the laminar assembly 312 so that air generated by the fans 308 flows through the plenum 310 and into the laminar assembly 312. The attachment mechanism 304 is configured to attach the device 300 to the user's upper chest and upper back, adjacent to the user's neck.

Figure 15A:
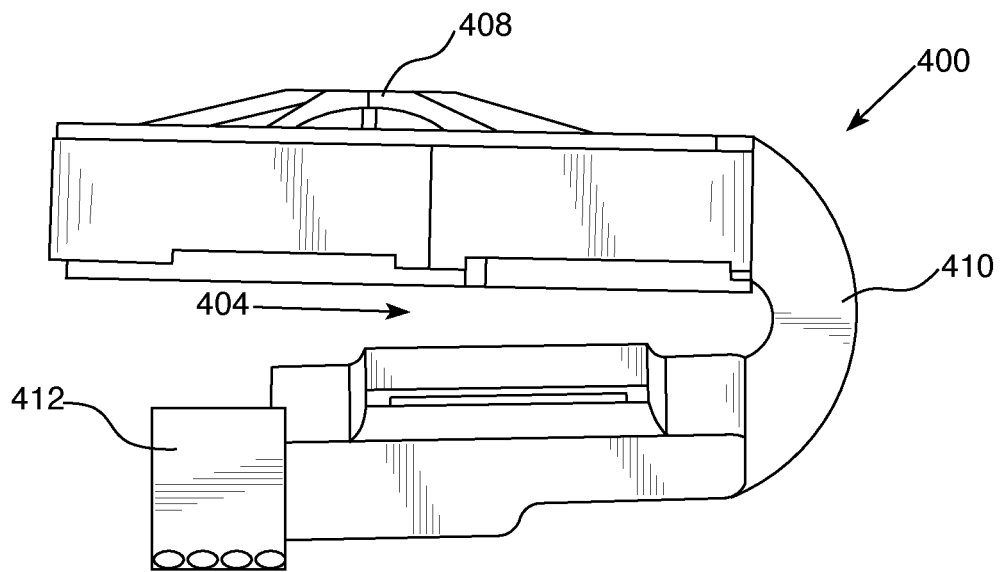
FIGS. 15A and 15B are side views of an airflow device by itself and in use attached to a hat brim, respectively, in accordance with an embodiment of the present invention.
Figure 15B:
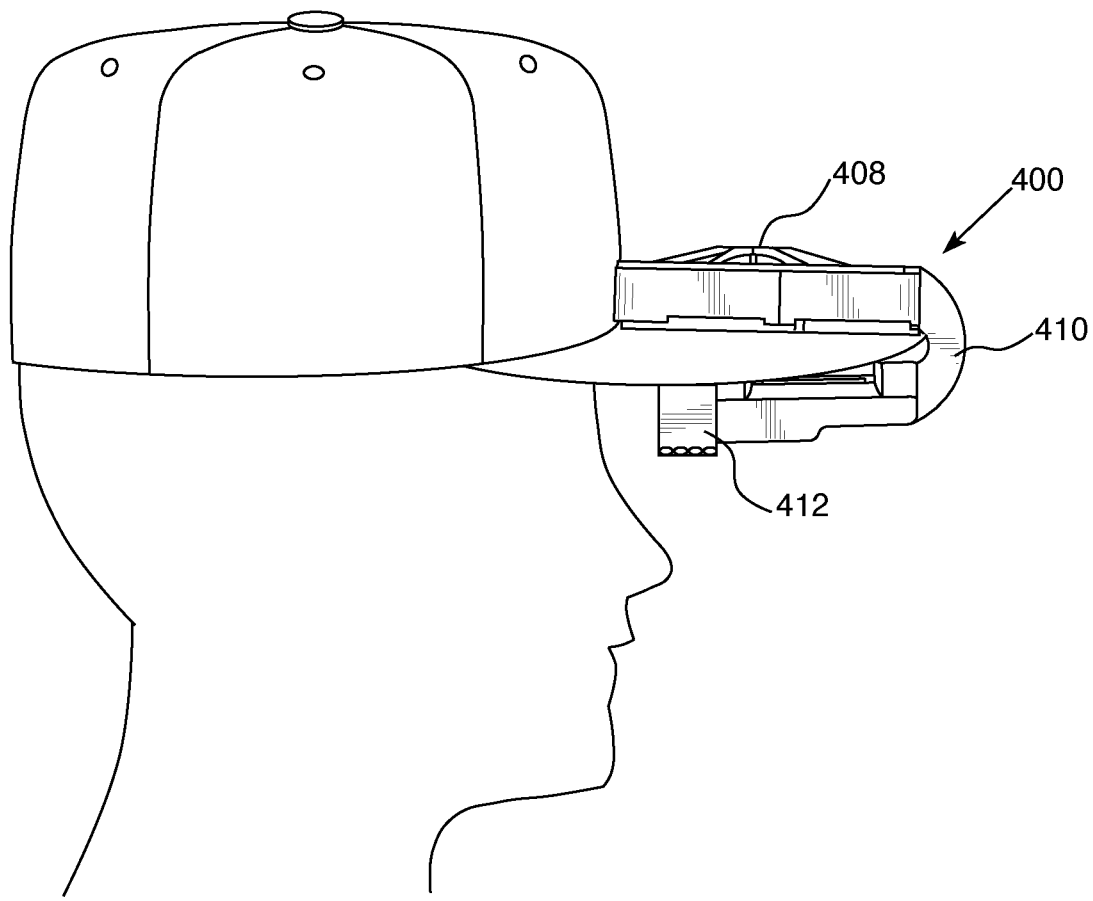

In one embodiment, shown in FIGS. 15A and 15B, the air shield device 400 is configured to clip onto a hat rather than being strapped around the user's head. The air shield device 400 includes fans 408, a plenum 410 and a laminar assembly 412. As shown in FIG. 15B, a user may clip the air shield device 400 to a hat having a brim so that the fan 408 is positioned atop the hat brim and the laminar assembly 412 is positioned below the hat brim. The plenum 410 curves around the hat brim and directs air generated by the fans 408 towards the laminar assembly 412. In this embodiment, the attachment mechanism 404 is a clip that clips the device 400 to the hat brim.

Figure 16A:
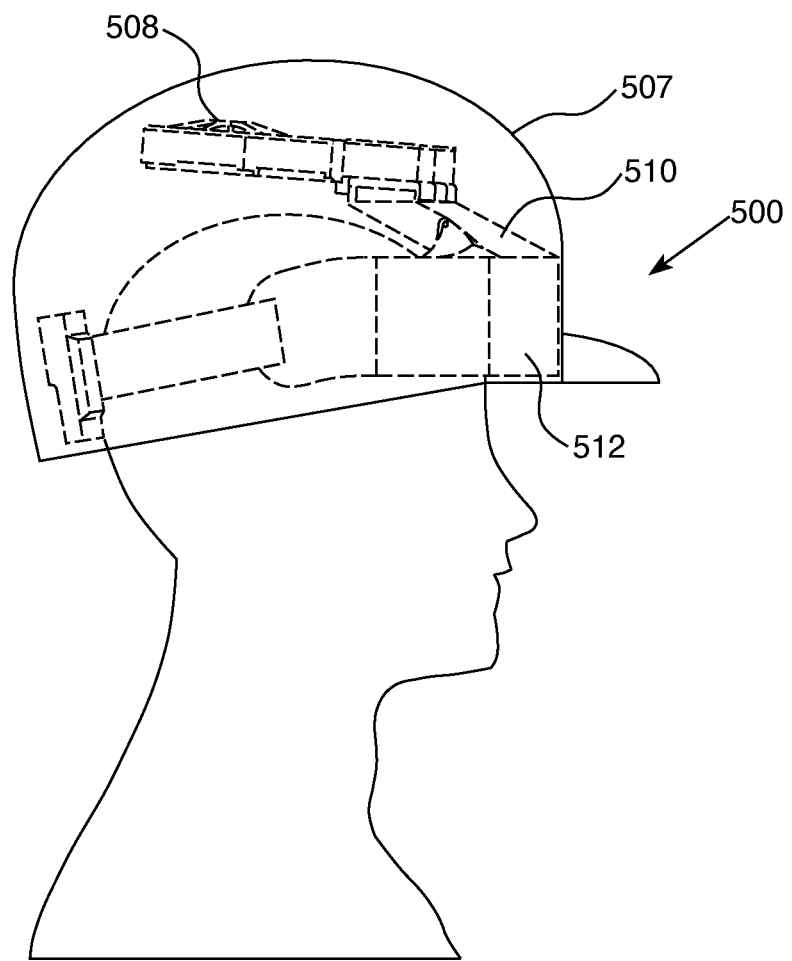
FIGS. 16A and 16B are side views of an airflow device attached to an inside of a helmet and an outside of a helmet, respectively, in accordance with embodiments of the present invention.
Figure 16B:
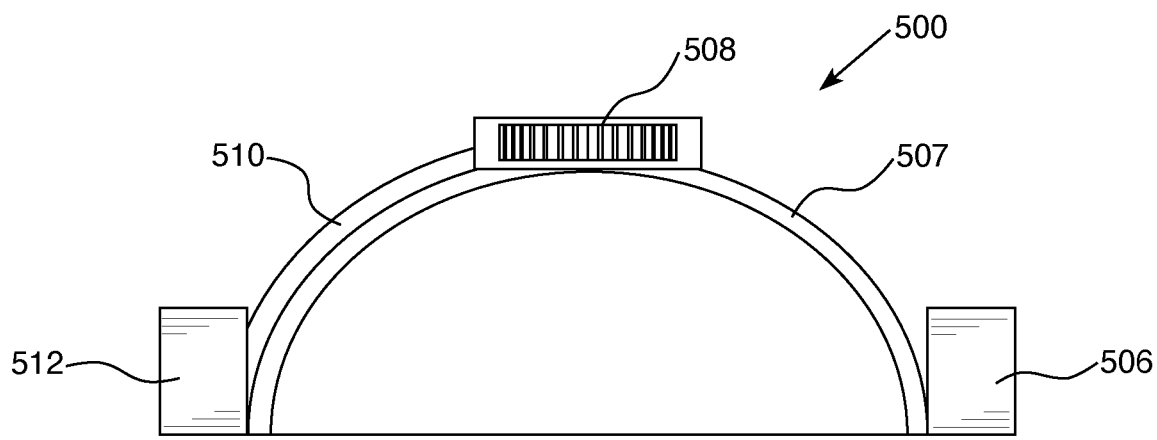

In another configuration, shown in FIGS. 16A and 16B, the air shield device 500 is built in to a helmet 507, such as a construction helmet, sports helmet, motorcycle helmet, or the like. In the configuration shown in FIG. 16A, the air shield device 500 is disposed almost entirely inside the helmet 507. In the configuration shown in FIG. 16B, the air shield device 500 is attached to the outer surface of the helmet 507 so that the fans 508 are positioned atop the helmet 507, the battery module 506 is attached to one side of the helmet, the laminar assembly 512 is attached to the other side of the helmet 507, and the plenum or air pathway 510 is positioned between the fans 508 and the laminar assembly 512. When a user wears the helmet 507, the laminar assembly 512 is positioned adjacent to the user's forehead and the laminar air sheet created by the air shield device 500 is positioned in front of the user's face. In the embodiments shown in FIGS. 16A and 16B, the attachment mechanism for attaching the device 500 to the user's head is the helmet 507.

Figure 17:
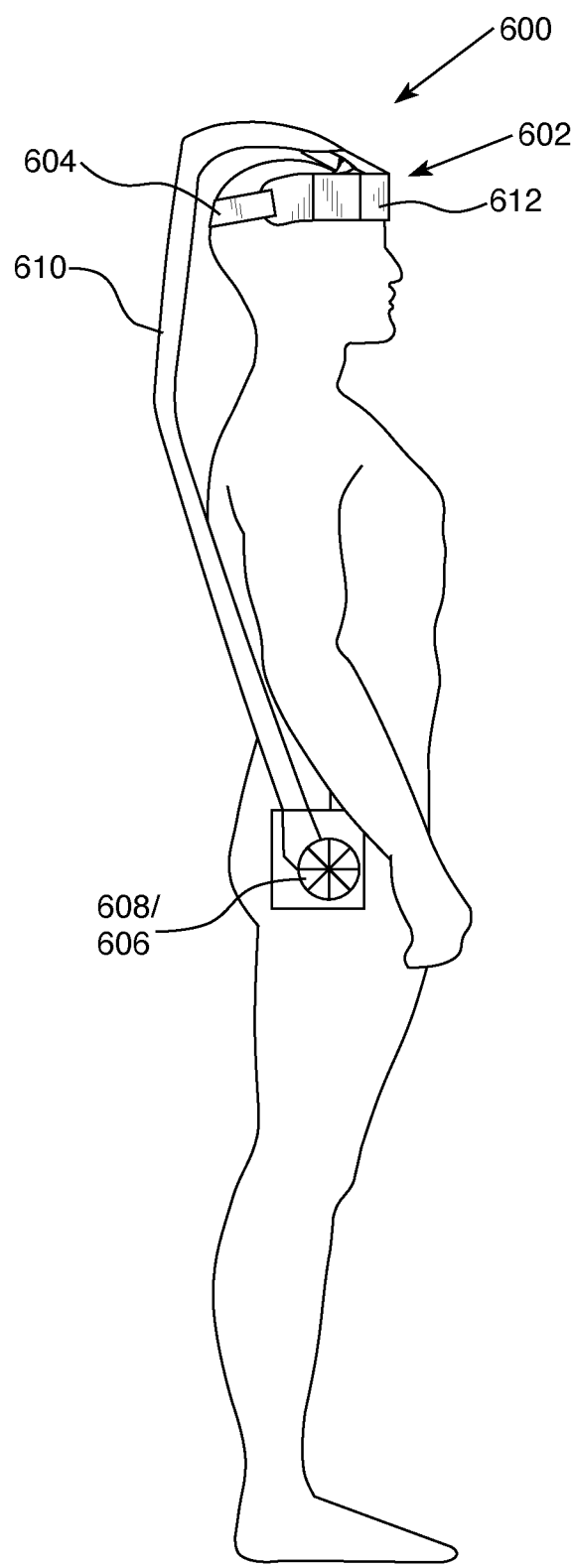
FIG. 17 is a side view of an airflow device in use attached to a user's head and waist, in accordance with an embodiment of the present invention.

In the configuration shown in FIG. 17, the air shield device 600 has components similar to the above embodiments arranged in a different configuration. Specifically, the fans 608 and power source 606 are worn around, or adjacent to a user's waist. An elongate tube 610 couples the fan 608 to a forehead assembly 602 that includes a laminar assembly 612. The forehead assembly 602 is strapped to the user's forehead with an attachment mechanism 604. Air generated by the fans 608 flows through the elongate tube 610, to the laminar assembly 612, which directs the air into a laminar flow air curtain in front of the user's face. The air shield device 600 may include a filter (not shown) that filters contaminants out of the air before the air reaches the laminar assembly 612. With this configuration, the weight of the portion of the device 600 strapped to the user's head is reduced, thereby improving the comfort of the user. One of ordinary skill in the art will readily appreciate that the laminar assembly 612 may alternatively be positioned under the user's chin, similar to the embodiments shown in FIGS. 13 and 14.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. An airflow device configured for creating an air barrier, wherein the airflow device comprises:
   at least one fan;
   a power source coupled to the at least one fan;
   a laminar assembly comprising a plurality of tubes, wherein the laminar assembly is coupled to the at least one fan so that air flow generated by the at least one fan passes through the plurality of tubes to create the air barrier, wherein each tube in the plurality of tubes has a diameter of 0.8 inches or less;
   an air passageway coupled to the at least one fan and the laminar assembly such that the air flow generated by the at least one fan passes through the air passageway before reaching the laminar assembly; and an attachment mechanism for attaching the laminar assembly to a user in a location near the user's head such that the air barrier created by the laminar assembly is positioned in front of the user's face.

2. The airflow device of claim 1, wherein the power source comprises a rechargeable battery.

3. The airflow device of claim 1, wherein the attachment mechanism is configured to attach the laminar assembly to a user's forehead, chest, or neck, or to a brim of a hat.

4. The airflow device of claim 1, wherein the at least one fan comprises two fans.

5. The airflow device of claim 1, wherein the diameter of each tube in of the plurality of tubes is 0.05 inches or more.

6. The airflow device of claim 3, wherein the attachment mechanism is a strap, a clip, or a helmet.

7. The airflow device of claim 1, wherein, when the airflow device is attached to the user, the at least one fan is positioned above the user's head, the laminar assembly is positioned against the user's forehead, and the air passageway is a plenum positioned between the at least one fan and the laminar assembly.

8. The airflow device of claim 1, wherein, when the airflow device is attached to the user, the at least one fan is positioned adjacent to the user's neck, the laminar assembly is positioned below the user's chin, and the air passageway is a plenum positioned between the at least one fan and the laminar assembly.

9. The airflow device of claim 1, further comprising an air treatment device for purifying the air used to create the air barrier.

10. The airflow device of claim 9, wherein the air treatment device comprises at least one of: a filter, a UV light emitter, an air ionizer, an electrostatic precipitator, and an impactor.

11. The airflow device of claim 1, further comprising a fan speed adjustment mechanism.

12. The airflow device of claim 1, further comprising an anemometer.

13. The airflow device of claim 1, further comprising a plastic shield adjacent to the air barrier.

14. The airflow device of claim 1, further comprising a copper mesh disposed in an intake of the fan.

15. The airflow device of claim 1, wherein each tube in the plurality of tubes has a length of at least 1.5 inches.

16. The airflow device of claim 1, wherein, when the airflow device is attached to the user, the at least one fan and the power supply are positioned adjacent to the user's waist, and the laminar assembly is positioned adjacent to the user's forehead or neck.

17. The airflow device of claim 16, wherein the air passageway coupled to the at least one fan and the laminar assembly is an elongate tube.

18. An airflow device configured for creating an air barrier, wherein the airflow device comprises:
at least one fan;
a power source coupled to the at least one fan;
a laminar assembly comprising a plurality of tubes, wherein the laminar assembly is coupled to the at least one fan so that air flow generated by the at least one fan passes through the plurality of tubes to create the air barrier, wherein the diameter of each tube in of the plurality of tubes is 0.05 inches or more;
an air passageway coupled to the at least one fan and the laminar assembly such that the air flow generated by the at least one fan passes through the air passageway before reaching the laminar assembly; and
an attachment mechanism for attaching the laminar assembly to a user in a location near the user's head such that the air barrier created by the laminar assembly is positioned in front of the user's face.

19. An airflow device configured for creating an air barrier, wherein the airflow device comprises:
at least one fan;
a power source coupled to the at least one fan;
a laminar assembly comprising a plurality of tubes, wherein the laminar assembly is coupled to the at least one fan so that air flow generated by the at least one fan passes through the plurality of tubes to create the air barrier;
an air passageway coupled to the at least one fan and the laminar assembly such that the air flow generated by the at least one fan passes through the air passageway before reaching the laminar assembly; and
an attachment mechanism for attaching the laminar assembly to a user in a location near the user's head such that the air barrier created by the laminar assembly is positioned in front of the user's face, wherein, when the airflow device is attached to the user, the at least one fan and the power supply are positioned adjacent to the user's waist, and the laminar assembly is positioned adjacent to the user's forehead or neck.

\* \* \* \* \*